(12) United States Patent
Lohmer et al.

(10) Patent No.: US 7,544,845 B2
(45) Date of Patent: Jun. 9, 2009

(54) PROCESS FOR TREATING PHENOL

(75) Inventors: Gunther Lohmer, Mulheim (DE); Otto Schnurr, Putte-Kapellen (BE); Manfred Weber, Haltern (DE); Markus Weber, Haltern (DE)

(73) Assignee: Ineos Phenol GmbH & Co. KG, Gladbeck (DE)

( * ) Notice: Subject to any disclaimer, the term of this patent is extended or adjusted under 35 U.S.C. 154(b) by 56 days.

(21) Appl. No.: 11/736,507

(22) Filed: Apr. 17, 2007

(65) Prior Publication Data

US 2007/0244345 A1   Oct. 18, 2007

Related U.S. Application Data

(60) Provisional application No. 60/793,116, filed on Apr. 18, 2006.

(51) Int. Cl.
*C07C 37/00* (2006.01)
(52) U.S. Cl. .................................... 568/800
(58) Field of Classification Search ............. 568/800
See application file for complete search history.

(56) References Cited

U.S. PATENT DOCUMENTS 3,029,294 A  4/1962  Keeble
5,414,154 A  5/1995  Jenczewski et al.
5,502,259 A  3/1996  Zakoshansky et al.
7,205,442 B2 * 4/2007  Payne ..................... 568/749

FOREIGN PATENT DOCUMENTS

DE  16 68 952 A1  11/1969
DE  73 326 A     5/1970
GB  1 231 991    5/1971

OTHER PUBLICATIONS

European Search Report from corresponding European Patent Application No. EP 06 00 7950, Aug. 25, 2006.

* cited by examiner

*Primary Examiner*—Daniel M Sullivan
*Assistant Examiner*—Kellette Gale
(74) *Attorney, Agent, or Firm*—Knobbe Martens Olson & Bear LLP

(57) ABSTRACT

The present invention relates to a continuous method for treating a crude phenol stream comprising methylbenzofuran and hydroxyacetone by passing the crude phenol stream through at least two reactors connected in series the reactors containing an acidic ion exchange resin, whereby the temperature in successive reactors decreases in flow direction of the phenol stream so that the temperature in the first reactor in flow direction of the phenol stream is between 100° C. and 200° C. and the temperature in the last reactor in flow direction of the phenol stream is between 50° C. and 90° C. without a thermal separation step between any of two successive reactors and to the use of this method in a process for making phenol.

20 Claims, 3 Drawing Sheets

PROCESS FOR TREATING PHENOL

CROSS-REFERENCE TO RELATED APPLICATIONS

This application claims priority to U.S. Provisional Application No. 60/793,116, filed Apr. 18, 2006, the disclosure of which is hereby incorporated by reference in its entirety.

BACKGROUND OF THE INVENTION

1. Field of the Invention

The present invention relates to a method for treating phenol, particularly to a continuous method for removing hydroxyacetone as well as methylbenzofuran from a crude phenol stream.

2. Description of the Related Art

The process for preparing phenol from cumene is well known. In this process cumene is at first oxidized by air oxygen to cumene hydroperoxide. This process step is typically called oxidation. In the second reaction step, the so-called cleavage, the cumene hydroperoxide is cleaved to phenol and acetone using a strong mineral acid as catalyst, for example sulfuric acid. The product from this second reaction step, the so-called cleavage product, is then fractionated by distillation.

The purity requirements for phenol to be marketed are becoming more and more stringent. Consequently, in order to operate a phenol production plant economically, overall yield and selectivity to the desired end product has to be improved and impurities formed during any of the above-described reaction steps have to be removed as quantitatively as possible with the lowest possible loss of the desired end product, especially phenol and acetone, at low investment and variable costs, especially energy costs. The predominant by-products formed in the oxidation steps are dimethylbenzyl alcohol and acetophenone. Acetophenone leaves the process with the high-boilers from the distillation. Dimethylbenzyl alcohol is dehydrated in the cleavage step to alpha-methylstyrene which partially forms high-boiling dimers and cumylphenols in the acid catalyst cleavage step. The high-boilers are separated from phenol in the distillation step. The unreacted alpha-methylstyrene is separated and hydrogenated in order to form cumene that is recycled into the process. Depending on the market demand, alpha-methylstyrene can also be further purified and sold as value product. Thus, one focus in the prior art is how to operate the oxidation step as well as the cleavage step in order to reduce the formation of these high-boilers which can be considered as direct cumene losses. For example for the cleavage these methods are described in U.S. Pat. No. 4,358,618, U.S. Pat. No. 5,254,751, WO98/27039 and U.S. Pat. No. 6,555,719.

But besides these high-boilers other components are formed in the cleavage, as for example hydroxyacetone, 2-methylbenzofuran and mesityloxide. These so-called micro impurities are not easy to separate from phenol in the distillation. Hydroxyacetone is the most critical component as it is nearly impossible to separate it from phenol by distillation. Hydroxyacetone is typically also the impurity with the highest concentration in the product obtained from the cleavage step. The concentration of hydroxyacetone in the cleavage product may vary between 200 and 3.000 wppm (weight parts per million).

Thus, there are great efforts in the prior art to remove and separate hydroxyacetone from the product obtained from the cleavage step (see for example U.S. Pat. No. 6,066,767, U.S. Pat. No. 6,630,608, U.S. Pat. No. 6,576,798 and U.S. Pat. No. 6,875,898). The disadvantage of all these methods is that high volume flows of cleavage product must be processed. In addition, in U.S. Pat. No. 6,875,898, the high volume flow of cleavage product must be treated with an oxidizing agent that may cause enormous efforts to operate the process safely.

Prior to distillation, the cleavage product is neutralized with a basic aqueous solution such as sodium phenate or caustic soda. The cleavage product which is saturated with water is then worked-up by distillation. A well known method is to separate most of the hydroxyacetone with an aqueous phase which is separated in the first distillation column while a crude phenol together with the high-boilers is taken as the bottom product, as described in U.S. Pat. No. 3,405,038 or in U.S. Pat. No. 6,657,087. In any case the crude phenol which will be further worked up in successive columns will still have concentrations of hydroxyacetone, 2-methylbenzofuran and mesityloxide of some 100 wppm which are not tolerable in pure phenol or even high purity phenol.

DE-AS 1 668 952 discloses a method to remove carbonyl-containing components, like mesityloxide, isomesityloxide, methylisobuylketone, hydroxyacetone and acetophenone, from crude phenol by passing the crude phenol over acidic ion exchange resins at temperatures between 45 and 200° C., preferably between 80 and 150° C.

This reference also discloses the possibility to use two different ion exchange resins whereby—when using such a catalyst combination—different temperatures can be used in order to optimize the efficiency for each catalyst type. This reference is totally silent with respect to the removal of methylbenzofuran nor does this reference disclose that reactors containing the ion exchange resin are operated using a well-defined temperature profile throughout the series of reactors.

As is evidenced by the introductory part of DE-A 199 51 373, the process disclosed in DE-AS 1 668 952 is not suitable to remove low activity carbonyl compounds like methylisobutylketone and methylcyclopentenone and compounds like methylbenzofuran. Consequently, the process described in DE-AS 1 668 952 does not solve the problem of removing hydroxyacetone as well as methylbenzofuran from a crude phenol stream.

In U.S. Pat. No. 5,414,154 a method for purification of phenol is described wherein a phenol stream is contacted with an ion exchange resin at temperatures between 70 and 120° C. It is emphasized in that patent that the effectiveness of the treatment with ion exchange resin increases with increasing temperature taking into account the range of temperature stability for the resin. But it is furthermore evident that methylbenzofuran can only be separated from the crude phenol stream if the initial hydroxyacetone concentration in the crude phenol stream is below 260 wppm and preferably hydroxyacetone is completely removed in order to have hydroxyacetone present in an amount of 10 wppm in order to effectively remove methylbenzofuran when contacting the crude phenol stream with the ion exchange resin.

Consequently, the process described in U.S. Pat. No. 5,414,154 requires an effective removal of hydroxyacetone in upstream units prior to the purification on the ion exchange resin. This is a disadvantage because any removal of hydroxyacetone in upstream units prior to the purification of the ion exchange resin means an extra effort in terms of investment costs and variable costs. Examples of such methods are described in U.S. Pat. No. 6,066,767, U.S. Pat. No. 6,630,608, U.S. Pat. No. 6,576,798 and U.S. Pat. No. 6,875,898.

DE-A 1 995 373, taking into account the disadvantages of DE-A 1 668 952 that 2-methylbenzofuran cannot be effectively separated by the method disclosed therein and the disadvantage of the teaching of U.S. Pat. No. 5,414,154 that methylbenzofuran can only be effectively removed from the crude phenol if the hydroxyacetone content of the crude phenol stream treated with the ion exchange resin is below a certain limit, suggests a two-step process of contacting the crude phenol stream with an ion exchange resin with a thermal separation step, like a distillation step, between the two steps of contacting the crude phenol with an acidic ion exchange resin. This method has the tremendous disadvantage that an additional distillation step is necessary which considerably increases the investment and energy costs of the entire process.

Finally, the teaching of US 2005/0137429 tries to avoid these disadvantages of multi-step purification of crude phenol in order to remove hydroxyacetone and methylbenzofuran by using a one-step process whereby the crude phenol is contacted with an ion exchange resin at low temperatures between 50 and 100° C. Although this one-step process is indeed effective in reducing the hydroxyacetone as well as the methylbenzofuran, this method need relatively high reactor volumes and/or highly activated ion exchange resins because of the lower reaction rate at this relatively low temperatures.

In view of the prior art as discussed above, there is still a need for an effective and economical method for purification of crude phenol to reduce hydroxyacetone as well as methylbenzofuran and other impurities in order to produce high purity phenol.

SUMMARY OF THE INVENTION

This object has been surprisingly attained by a continuous method for treating a crude phenol stream comprising methylbenzofuran and hydroxyacetone by passing the crude phenol stream through at least two reactors connected in series the reactors containing an acidic ion exchange resin, whereby the temperature in successive reactors decreases in flow direction of the phenol stream so that the temperature in the first reactor in flow direction of the phenol stream is between 100° C. and 200° C. and the temperature in the last reactor in flow direction of the phenol stream is between 50° C. and 90° C. without a thermal separation step between any of two successive reactors.

Contrary to the teachings of the prior art references the present inventors have realized that by using a plurality of reactors containing the acidic ion exchange resin in series and importantly adjusting a temperature profile throughout the series of reactors as defined above a crude phenol stream can be purified to a low content of hydroxyacetone as well as methylbenzofuran without initially removing hydroxyacetone prior to contact with the acidic ion exchange resin and without an energy-consuming distillation step between two reactors comprising the acidic ion exchange resin. Furthermore surprisingly, although at least two reactors have to be used, the overall weight hourly space velocity of the process according to the present invention is considerably higher than for the one-step process described in US 2005/0137429 with the effect that the total reactor volume required according to the present invention is even lower than for the one-step process, as disclosed in US 2005/0137429.

The process for treating a crude phenol stream can be easily integrated into a process for preparation of phenol. Thus, the present invention also relates to a process for preparation of phenol comprising:

a) oxidizing cumene to form an oxidation product containing cumene hydroperoxide;

b) cleaving said oxidation product using an acidic catalyst to form a cleavage product containing phenol, acetone and impurities;

c) separating said cleavage product into a plurality of product streams, one of said product streams is a crude phenol stream comprising hydroxyacetone and methylbenzofaran;

d) treating said crude phenol stream with the method as defined above to form a treated phenol stream reduced in hydroxyacetone and methylbenzofuran; and e) subjecting said treated phenol stream to a distillation to obtain a purified phenol.

DETAILED DESCRIPTION OF THE PREFERRED EMBODIMENT

Figure 1:
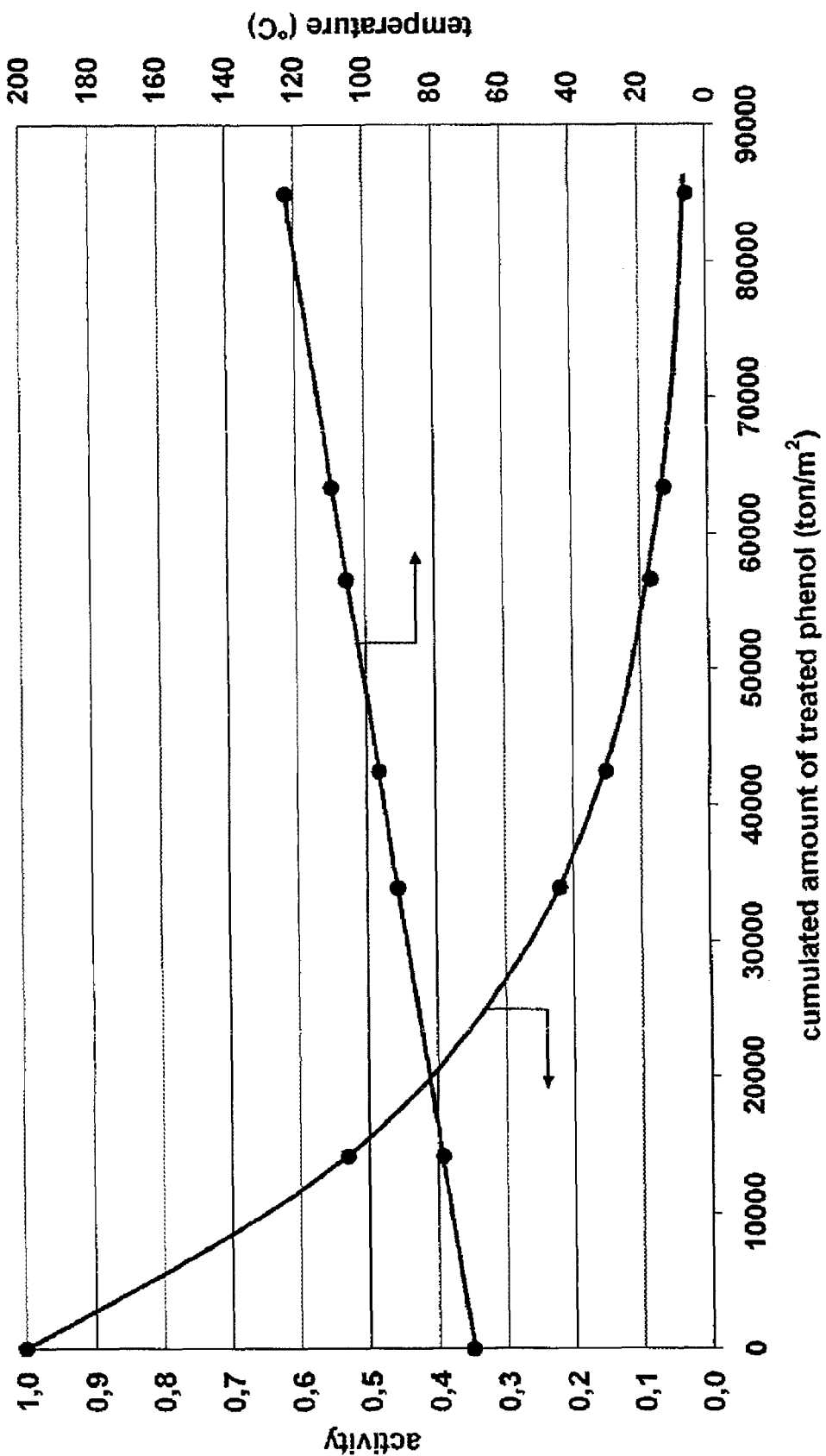
FIG. 1 shows the function of catalyst activity and reactor temperature dependent on catalyst utilization as determined in example 1.

The crude phenol that can be effectively purified by the process of the present invention contains as impurities predominantly hydroxyacetone as well as methylbenzofuran. The concentration of hydroxyacetone can be up to 1,000 wppm and the concentration of methylbenzofuran can be up to 200 ppm. One advantage of the present invention is that hydroxyacetone as well as methylbenzofuran can be effectively removed even if the hydroxyacetone concentration is more than 260 wppm. Thus, a crude phenol stream comprising up to 1,000 wppm, preferably more than 260 wppm to 1,000 wppm hydroxyacetone and up to 200 wppm, preferably 50 to 200 wppm methylbenzofuran can be successfully purified.

In addition to hydroxyacetone and methylbenzofuran further impurities may be present:
Mesityloxide up to 1,000 wppm,
2-phenylpropionaldehyde up to 500 wppm,
methylisobutylketone up to 500 wppm,
acetophenone up to 500 wppm,
3-methylcyclohexanone up to 500 wppm,
alpha-methylstyrene up to 2,000 wppm,
phenylbutenes up to 1,000 wppm.

These concentration ranges cover the relevant concentrations of these components in crude phenol which is separated from acetone, cumene and alpha-methylstyrene, water and high-boilers by distillation prior to the purification on an ion exchange resin.

When contacting the crude phenol stream with the acidic ion exchange resin hydroxyacetone and methylbenzofuran react to high-boilers. Mesityloxide reacts with phenol to high-boilers and water. In the presence of water, which is also formed by the reaction between hydroxyacetone and phenol, parts of the mesityloxide may decompose to acetone on the acidic ion exchange resin. Acetone may further react with phenol to Bisphenol A. Besides hydroxyacetone and mesityloxide there are other carbonylic components which may still be present in the phenol in small amounts, like phenylpropionaldehyde, methylisobutylketone, acetophenone and 3-methylcyclohexanone. In addition, the phenol may have final traces of unsaturated hydrocarbons, like alpha-methylstyrene and phenolbutenes which are undesirable components in purified phenol. Like the carbonyl-containing components, the unsaturated hydrocarbons form high-boilers with phenol when in contact with acidic ion exchange resins. It was found that, even if these other impurities are present in impure phenol, the conversion of hydroxyacetone and methylbenzofuran is not adversely effected. Furthermore, the conversion of these additional impurity components to high-boilers is always completed when the conversion of hydroxyacetone and methylbenzofaran is completed. Consequently, the process of the present invention allows for the conversion of all the undesired impurities in crude phenol to high-boilers that can be easily removed from the purified phenol in a final distillation step after the crude phenol has been contacted with the acidic ion exchange resin according to the process according to the present invention.

After contact of the crude phenol with the acidic ion exchange resin, final concentration of hydroxyacetone of less than 1 wppm and concentrations of methylbenzofuran of less than 20 wppm, preferably less than 10 wppm, can be obtained. As mentioned above, all other impurities are quantitatively converted to high-boilers. Therefore, the process according to the present invention is well suited to prepare high purity phenol. The number of reactors containing the acidic ion exchange resin connected in series and, thus, the number of different temperature levels according to the present invention is not particularly restricted, but taking into account economic considerations in terms of investment costs and variable costs, a number of two to four reactors connected in series is preferred whereby two reactors connected in series are most preferred. Thus, according to this most preferred embodiment, the process is conducted at two distinguished temperature levels.

As will be explained in more detail in the examples the present inventors have found that the deactivation of commercial ion exchange resin correlates very well with the degree of utilization. The degree of utilization is defined as the total amount of treated phenol which was contacted with the ion exchange resin during a certain period of time. For a continuous plug flow reactor this is the total amount of treated phenol per cross-sectional area of the reactor.

After a high degree of utilization the activity of the catalyst is only some percent of that of the fresh catalyst. Surprisingly the temperature, that is necessary to compensate the deactivation at a constant weight hourly space velocity (WHSV), increases proportional to the degree of utilization, as shown in FIG. 1. From practical considerations the maximal temperature is 200° C. in order to avoid any thermal degradation of commercial ion exchange resins.

On the other hand it was found that for a phenol stream comprising methylbenzofuran as well as considerably amounts of hydroxyacetone e.g., up to 200 wppm methylbenzofaran and up to 1000 wppm hydroxyacetone a temperature in the last reactor below 90° C. is necessary to obtain a residual amount of methylbenzofuran below 20 wppm, preferably below 70° C. to obtain a residual amount of methylbenzofuran below 10 wppm. From practical considerations the temperature should not be below 50° C. in order to avoid a too high reactor volume even with fresh catalyst.

One advantage of having a plurality of distinct temperature levels for the contact of crude phenol with the acidic ion exchange resin is that used or partly used acidic ion exchange resin can be contacted at relatively high temperatures that for example favor the conversion of hydroxyacetone, but not the conversion of methylbenzofuran, with the result that even with a used or partly used catalyst due to the high temperatures a high activity of the already spent catalyst can be maintained. On the other hand, at the low temperature level fresh or only partly used catalyst can be employed at low temperatures favoring the conversion of methylbenzofuran and since the catalyst is still relatively fresh, high catalyst activity can be obtained even at low temperatures. Consequently, an optimum balance of selectivity of the contact with the acidic ion exchange resin can be obtained while at the same time assuring optimum activity of the catalyst resulting in comparatively high weight hourly space velocity thereby reducing the necessary catalyst volume for treatment of a specific phenol stream.

This synergistic effect of optimization of catalyst selectivity with respect to hydroxyacetone and methylbenzofuran and catalyst activity depending on the grade of deactivation of the catalyst by using the claimed temperature profile was neither known nor derivable from the prior art.

A further advantage of the present invention is that if several reactors are connected in series, including at least one spare reactor, in a continuous process completely spent catalyst can be easily removed from the process line. The reactor with the most spent catalyst which is at the highest temperature level and, thus, at the upstream end can be disconnected from the line, and the reactor with fresh catalyst will enter the line at the lowest temperature level, thus at the downstream end of the line. In the reactor that is disconnected from the line, the spent catalyst will be either substituted by fresh catalyst or regenerated in a separate process step in order to retain the initial activity of the fresh catalyst. This reactivated reactor can then enter the line at the lowest temperature level as soon as the reactor at the highest temperature level, wherein the catalyst has been deactivated to an undesirable level, is removed from the line. This allows for a continuous process wherein the efficiency of the purification is approximately constant over the time resulting in a product of almost constant specification which is extremely important for a high volume product as phenol.

It is preferred to use reactors of the same size. Thus, at each position in the line, the WHSV for a certain phenol stream is the same and does not change while changing the positions of the reactors in the line. The necessary temperatures in the reactors with ion exchange resins of different activities can easily determined by FIG. 1.

Furthermore, a plurality of reactors connected in parallel can be used for every temperature level. Thus, it is very easy to adapt the treating process to a changing throughput. Again it is preferred to use reactors of the same size and the same number of reactors at each temperature level.

Additionally, it is possible to use a heat integration of the phenol stream going through the reactors in order to minimize energy consumption. For example, the phenol stream can be passed through a heat exchanger between a first reactor and a successive second reactor using a colder phenol effluent from a reactor located downstream from the first reactor as coolant in the heat exchanger. This embodiment allows to cooling down the phenol stream between two successive reactors whereas at the same time the phenol stream leaving the last reactor at the lowest temperature level, when used as a coolant in the heat exchanger, is heated up so that the energy consumption in the subsequent distillation step to remove the high-boilers is reduced.

Furthermore, additional heat exchangers can be used between two successive reactors employing conventional coolants like cooling water to adjust the temperature of the phenol stream to the desired level.

According to one embodiment of the present invention, elongated vessels are used as reactors whereby the vessels are preferably arranged in a vertical orientation whereby the phenol flows from the top to the bottom of the reactor. But it is also possible to use an upstream flow in vertical vessels or to use horizontal vessels.

According to a preferred embodiment of the present invention, the reactors contain the acidic ion exchange resin in a fixed bed. Preferably, the superficial liquid velocity in the fixed bed of the ion exchange resin is 0.5 to 5 mm/sec, preferable 1.0 to 3.0 mm/sec and more preferred 1.5 to 2 mm/sec.

Any acidic ion exchange resin can be used as the catalyst according to the present invention. As used herein, the term "acidic ion exchange resin" refers to a cation exchange resin in the hydrogen form wherein the hydrogen ions are bound to the active sides which can be removed either by dissociation in solution or by replacement with other positive ions. The active sides of the resins have different attractive strengths for different ions and this selective attraction serves as means for ion exchange. Non-limiting examples of suitable acidic ion exchange resins include the series of sulfonated divinylbenzene crosslinked styrene copolymers, such as for example Amberlyst 16, commercially available from Rohm & Haas, K2431, commercially available from Lanxess, CT-151, commercially available from Purolite.

Other suitable resins can be commercially obtained from producers such as Lanxess, Rohm and Haas Chemical Company and Dow Chemical Company.

The key point of the present invention is to use a certain temperature profile throughout the series of reactors containing the acidic ion exchange resin as defined above. According to the present invention, the temperature in the first reactor in flow direction of the phenol stream is at least 100° C. and temperature of the last reactor in flow direction of the phenol stream is less than 90° C., preferably less than 70° C.

The temperature in the first reactor in flow direction of the phenol stream is 200° C. at most, preferably 150° C. at most, and most preferred 120° C. at most. The temperature in the last reactor in flow direction of the phenol stream is at least 50° C.

The invention will now be described in more detail with reference to specific embodiments shown in the attached figures.

FIG. 1 shows the function of catalyst activity and reactor temperature dependent on catalyst utilization as determined in example 1.

Figure 2:
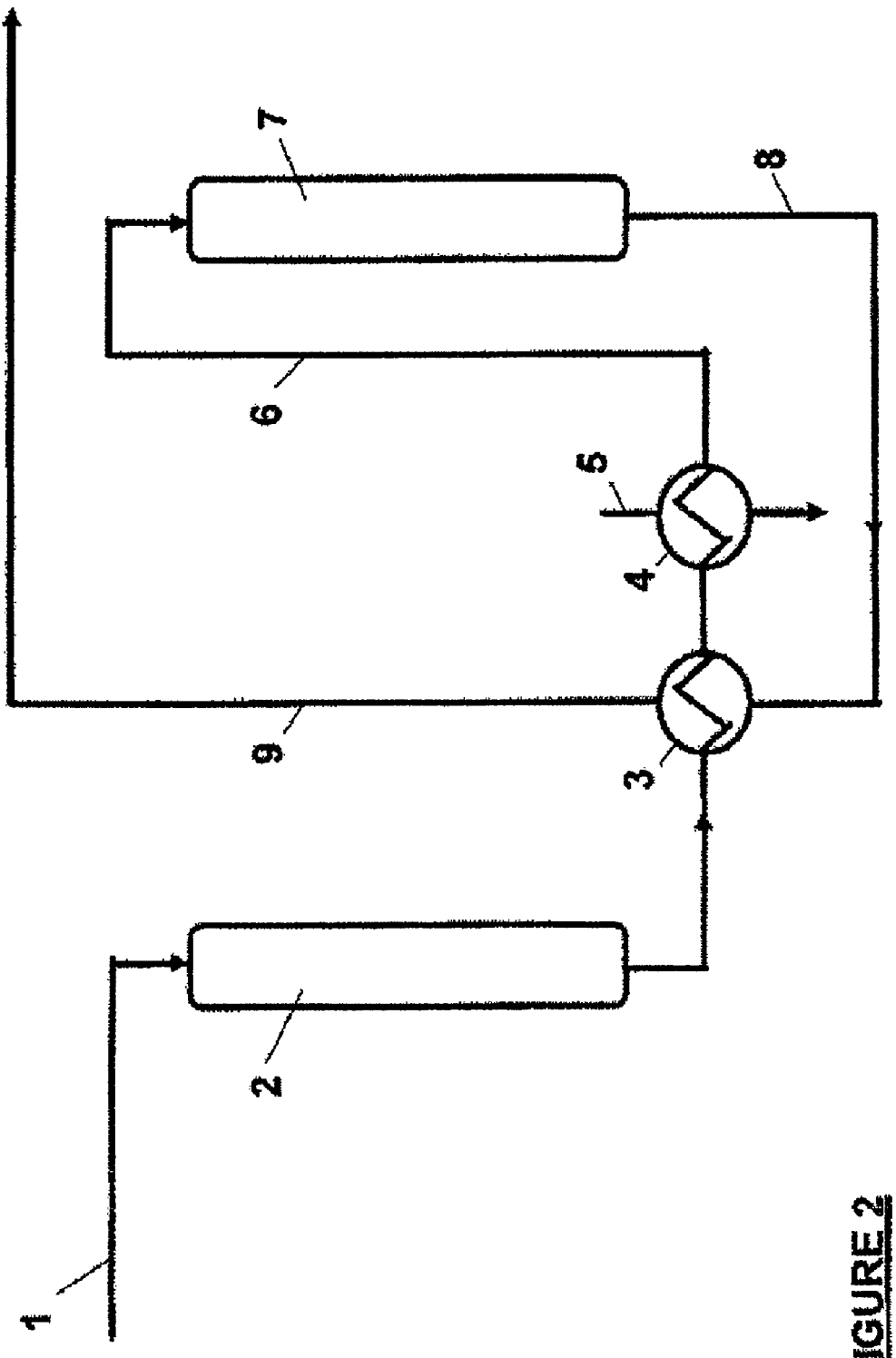
FIG. 2 exhibits a diagrammatic illustration of one embodiment according to the present invention with two reactors connected in series.

FIG. 2 exhibits a diagrammatic illustration of one embodiment according to the present invention with two reactors connected in series.

Figure 3:
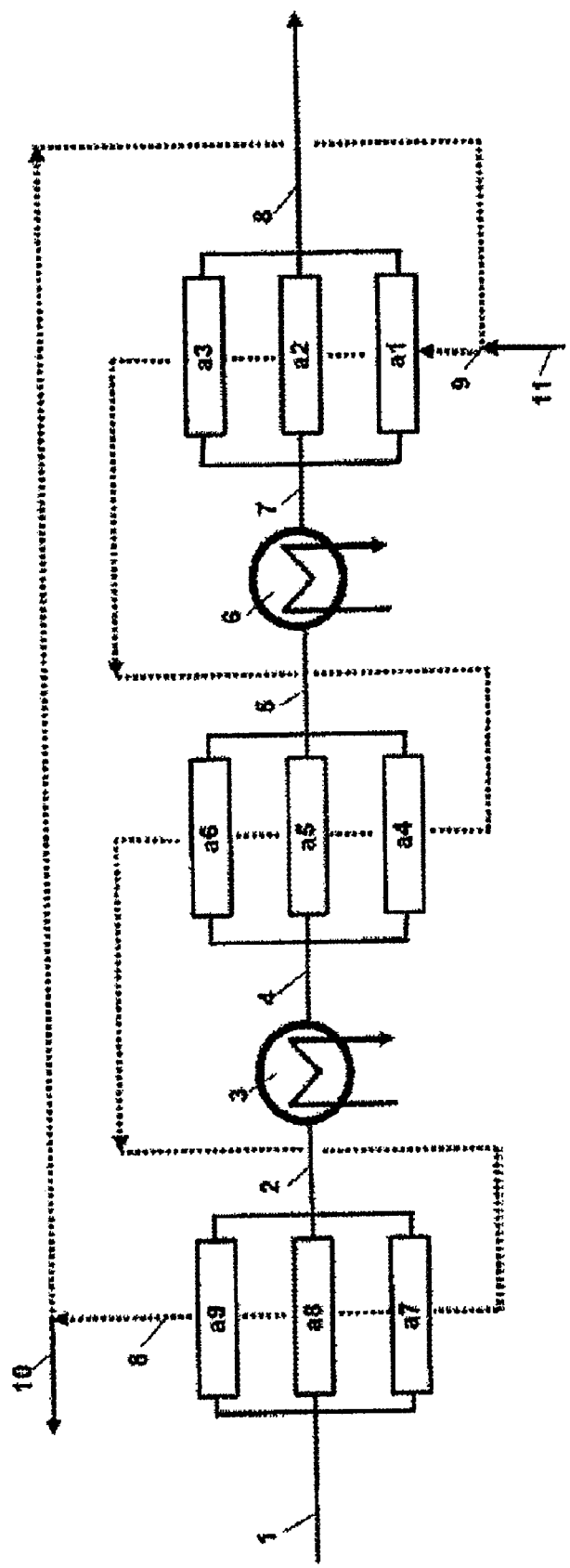
FIG. 3 shows an alternative embodiment of the present invention with three groups of three parallel reactors connected in series.

FIG. 3 shows an alternative embodiment of the present invention with three groups of three parallel reactors connected in series.

Referring to FIG. 2 impure phenol is passed through a fixed bed reactor 2 which is filled with an acidic ion exchange resin. The temperature can be up to 200° C. After leaving the first reactor the phenol is cooled down in the heat exchanger 3 with colder phenol 8 from the outlet of the second reactor 7. The phenol is finally cooled down to the desired low temperature in heat exchanger 4 using a suitable cooling stream 5, as for example water or any other process stream which allows to cool down the phenol, but avoid any crystallization of the phenol in the pipe system. The final temperature of phenol 6 is at least 50° C. Phenol 6 is then passed over the second reactor 7 to complete conversion of all relevant impurities. The phenol stream 9 is sent to a final distillation column to separate the high-boilers which are formed during the treatment on the acidic ion exchange resin in reactors 2 and 7. Because of the flexibility in temperature relatively high amounts of hydroxyacetone in addition to methylbenzofuran are tolerable in the feed even when using spent resins with low activity in the first reactor. This will be illustrated in the examples below in more detail.

Referring to FIG. 3 impure phenol 1 is passed through three reactors a7 to a9 in parallel at a high temperature. The phenol from these reactors is recombined to the stream 2 and cooled down to an intermediate temperature in the heat exchanger 3. The phenol 4 is again treated in three parallel reactors a4 to a6. The phenol from these reactors is recombined to the stream 5 and cooled to the final temperature in the heat exchanger 6. Phenol 7 is finally treated at the lowest temperature in the three parallel reactors a1 to a3. Phenol stream 8 is sent to a final distillation column to separate the high-boilers which are formed during the treatment of the acidic ion exchange resin in reactors a1 to a9. The resins in reactors a1 to a3 have the highest activity. The resins in the reactors a4 to a6 have a medium activity and the resins in the resins in the reactors a7 to a9 have the lowest activity. Consequently, after a certain period of time of utilization of the resin, the position of the reactors a1 to a3 will be successively changed to the middle row and the position of the reactors a4 to a6 will be successively changed to the left row, as indicated by the broken line. The waste resin 10 from the reactors a7 to a8 will be regenerated or discharged. The reactors a7 to a9 containing regenerated or refilled fresh resin 11 are positioned to the right row as shown by the broken line. These changes in reactor sequences can easily be done by using an interconnecting piping network between all reactors including spare reactors. As shown in FIG. 2, any heat integration between colder and warmer phenol streams is of course possible in reactor sequences as shown in FIG. 3.

In order to demonstrate the beneficial effects of the present invention the following examples are given.

EXAMPLES

Example 1

An impure phenol stream of 1 kg/h with 200 wppm hydroxyacetone is treated on an ion exchange resin type K2431 from Lanxess. The plug flow reactor has a diameter of 0.025 m and a height of 1.2 m. Thus the weight hourly space velocity WHSV (tons of phenol per hour and per $m^3$) in the plug flow reactor was 1.7. The temperature was adjusted to get a final concentration of about 10 wppm hydroxyacetone after the treatment. Fresh catalyst as well as catalyst samples from a production unit with different degrees of utilization were used. FIG. 1 shows the temperature which is necessary to compensate the deactivation with regard to the conversion of hydroxyacetone. The activity of the fresh catalyst maybe defined as "1.0". A temperature of 70° C. is sufficient to convert the hydroxyacetone from 200 to 10 wppm on this fresh ion exchange resin. The temperature must be increased to get the same conversion on ion exchange resins which are partly used. For example the temperature must be increased to 123° C. to get the same conversion of hydroxyacetone on an ion exchange resin which has a cumulated amount of phenol of around 85000 t/$m^2$.

Comparative Example 1

Impure phenol containing 1,000 wppm hydroxyacetone and 200 wppm methylbenzofuran is continuously treated on a fresh fixed bed ion exchange resin CT 151 from Purolite at 120° C. The weight hourly space velocity WHSV is 3.3. After the purification step the concentration of hydroxyacetone is <1 wppm, but the concentration of methylbenzofuran is 78 wppm and so too high. This concentration of methylbenzofuran cannot be further reduced at this temperature by adding a successive reactor, what means decreasing the WHSV.

Comparative Example 2

The impure phenol according to comparative example 1 is continuously treated on a fresh fixed bed ion exchange resin CT 151 from Purolite at 70° C. The weight hourly space velocity WHSV must be 0.7 to get final concentrations of hydroxyacetone to <1 wppm and for methylbenzofuran to <10 wppm.

Example 2

The impure phenol according to comparative example 1 using an apparatus according to FIG. 2 is at first continuously treated on a fresh fixed bed ion exchange resin CT 151 from Purolite at 120° C. with a weight hourly space velocity WHSV of 10. After the reactor the phenol is cooled down to 70° C. and continuously treated on a fresh fixed bed ion exchange resin CT 151 from Purolite at 70° C. with a weight hourly space velocity WHSV of 2. The final concentration of hydroxyacetone is <1 wppm and for methylbenzofuran <10 wppm. In comparison with comparative example 2, the same specification with a methylbenzofuran concentration <10 wppm is achieved with less than half of the reaction volume in total.

Example 3

Similarly to example 2 the impure phenol according to comparative example 1 is at first continuously treated on a fixed bed ion exchange resin CT 151 from Purolite at 120° C. The activity is only 20% compared to a fresh ion exchange resin. The weight hourly space velocity WHSV is 2. Then the phenol is cooled down to 70° C. and continuously treated on a fresh fix bed ion exchange resin at 70° C. with a weight hourly space velocity WHSV of 2. The final concentration of hydroxyacetone is <1 wppm and for methylbenzofuran 10 wppm. In comparison with comparative example 2, the same specification with a methylbenzofuran concentration <10 wppm is achieved with only 70% of the total reaction volume. In addition, again comparing to comparative example 2, half of the total reactor volume is filled with a resin having a low activity of only 20% compared to a fresh resin, thus allowing a much longer and therefore much higher economical usage of the ion exchange resin.

What is claimed is:

1. A continuous method for treating a crude phenol stream comprising methylbenzofuran and hydroxyacetone said method comprising passing the crude phenol stream through at least two reactors connected in series, the reactors containing an acidic ion exchange resin, whereby the temperature in successive reactors decreases in a flow direction of the phenol stream so that the temperature in the first reactor in the flow direction of the phenol stream is between 100° C. and 200° C. and the temperature in the last reactor in the flow direction of the phenol stream is between 50° C. and 90° C. without a thermal separation step between any of two successive reactors.

2. The method of claim 1, wherein 2 to 4 reactors connected in series are employed.

3. The method of claim 2, wherein the number of reactors is 2.

4. The method of claim 1, wherein at each temperature level a plurality of reactors are connected in parallel.

5. The method of claim 1, wherein the temperature in the first reactor in flow direction of the phenol stream is between 100° C. and 150° C.

6. The method of claim 5, wherein the temperature in first reactor in flow direction of the phenol stream is between 100° C. and 120° C.

7. The method of claim 1, wherein the temperature in the last reactor in flow direction of the phenol stream is between 50° C. and 70° C.

8. The method of claim 1, wherein the initial concentration of hydroxyacetone in the crude phenol stream is 0 to 1000 wppm.

9. The method of claim 8, wherein the initial concentration of hydroxyacetone in the crude phenol stream is 260 wppm to 1000 wppm.

10. The method of claim 1, wherein the initial concentration of methylbenzofuran in the crude phenol stream is 0 wppm to 200 wppm.

11. The method of claim 10, wherein the initial concentration of methylbenzofuran in the crude phenol stream is 50 wppm to 200 wppm.

12. The method of claim 1, wherein the crude phenol stream further comprises less than 1000 wppm mesityloxide, less than 500 wppm 2-phenylpropionaldehyde, less than 500 wppm methylisobutylketone, less than 500 wppm acetophenone, less than 500 wppm 3-methylcyclohexanone, less than 2000 wppm alpha-methylstyrene and less than 1000 wppm phenylbutene.

13. The method of claim 1, wherein the reactors contain the acid ion exchange resin in fixed bed arrangement.

14. The method of claim 1, wherein a superficial liquid velocity in the fixed bed of the ion exchange resin is 0.5 to 5 mm/s.

15. The method of claim 14, wherein the superficial liquid velocity in the fixed bed of the ion exchange resin is 1.0 to 3.0 mm/s.

16. The method of claim 14, wherein the superficial liquid velocity in the fixed bed of the ion exchange resin is 1.5 to 2 mm/s.

17. The method of claim 1, wherein the reactors are elongated vessels in vertical orientation.

18. The method of claim 17, wherein the phenol stream flows from the top to the bottom of the vessel.

19. The method of claim 1, wherein the phenol stream is passed through a heat exchanger between a first reactor and a successive second reactor using a colder phenol effluent from a reactor located downstream from the first reactor as coolant in the heat exchanger.

20. A method for producing phenol comprising:
a) oxidizing cumene to form an oxidation product containing cumene hydroperoxide;
b) cleaving said oxidation product using an acidic catalyst to form a Cleavage product containing phenol, acetone and impurities;
c) separating said cleavage product into a plurality of product streams, one of said product streams is a crude phenol stream comprising hydroxyacetone and methylbenzofuran;
d) treating said crude phenol stream with the method according to claim 1 to form a treated phenol stream reduced in hydroxyacetone and methylbenzofuran; and
e) subjecting said treated phenol stream to a distillation to obtain a purified phenol.

* * * * *

UNITED STATES PATENT AND TRADEMARK OFFICE
CERTIFICATE OF CORRECTION

PATENT NO. : 7,544,845 B2          Page 1 of 1
APPLICATION NO. : 11/736507
DATED : June 9, 2009
INVENTOR(S) : Lohmer et al.

It is certified that error appears in the above-identified patent and that said Letters Patent is hereby corrected as shown below:

On Title page (Item 75), for the first listed Inventor's address, please delete "Mulheim" and insert therefore, --Mülheim--.

At column 2, line 21, please delete "methylisobuylketone" and insert therefore, --methylisobutylketone,--.

At column 4, line 3, please delete "methylbenzofaran;" and insert therefore, --methylbenzofuran;--.

At column 4, line 30, please delete "ppm." and insert therefore, --wppm.--.

At column 5, line 7, please delete "methylbenzofaran" and insert therefore, --methylbenzofuran--.

At column 5, lines 49-50, please delete "methylbenzofaran" and insert therefore, --methylbenzofuran--.

At column 10, line 53, please delete "Cleavage" and insert therefore, --cleavage--.

Signed and Sealed this

Ninth Day of February, 2010

David J. Kappos
*Director of the United States Patent and Trademark Office*